(12) United States Patent
Annangi et al.

(10) Patent No.: US 11,488,298 B2
(45) Date of Patent: Nov. 1, 2022

(54) SYSTEM AND METHODS FOR ULTRASOUND IMAGE QUALITY DETERMINATION

(71) Applicant: GE Precision Healthcare LLC, Milwaukee, WI (US)

(72) Inventors: Pavan Kumar V. Annangi, Bangalore (IN); Hariharan Ravishankar, Bangalore (IN); Tore Bjaastad, Molde (NO); Erik Normann Steen, Moss (NO)

(73) Assignee: GE Precision Healthcare LLC, Milwaukee, WI (US)

( * ) Notice: Subject to any disclaimer, the term of this patent is extended or adjusted under 35 U.S.C. 154(b) by 215 days.

(21) Appl. No.: 16/723,718

(22) Filed: Dec. 20, 2019

(65) Prior Publication Data

US 2021/0192720 A1    Jun. 24, 2021

(51) Int. Cl.
*G06T 7/00* (2017.01)
*A61B 8/08* (2006.01)

(52) U.S. Cl.
CPC .......... *G06T 7/0012* (2013.01); *A61B 8/5207* (2013.01); *G06T 2207/10132* (2013.01); *G06T 2207/20182* (2013.01); *G06T 2207/30168* (2013.01)

(58) Field of Classification Search
CPC ........ G06T 7/0012; G06T 2207/20182; G06T 2207/10132; G06T 2207/30168; A61B 8/5207; A61B 8/58; A61B 8/483; A61B 8/488; A61B 8/486; A61B 8/0883
USPC ........................................... 382/128
See application file for complete search history.

(56) References Cited

U.S. PATENT DOCUMENTS

| | | | |
|---|---|---|---|
| 8,235,905 B2* | 8/2012 | Lin | A61B 8/14 600/458 |
| 2016/0310111 A1* | 10/2016 | Cho | A61B 8/54 |
| 2018/0214134 A1* | 8/2018 | Kim | A61B 8/4405 |
| 2018/0246208 A1* | 8/2018 | Dittmer | G01S 7/52084 |
| 2018/0306919 A1* | 10/2018 | Van Rens | G01S 7/52073 |
| 2018/0310920 A1* | 11/2018 | Specht | A61B 8/469 |
| 2019/0282208 A1* | 9/2019 | Silberman | A61B 8/468 |

(Continued)

FOREIGN PATENT DOCUMENTS

EP        1097674 A2    5/2001

OTHER PUBLICATIONS

Rangaraju, K. et al., "Review Paper on Quantitative Image Quality Assessment—Medical Ultrasound Images," International Journal of Engineering Research & Technology (IJERT), vol. 1, No. 4, Jun. 2012, 6 pages.

(Continued)

*Primary Examiner* — Van D Huynh
(74) *Attorney, Agent, or Firm* — McCoy Russell LLP

(57) ABSTRACT

Methods and systems are provided for improving image quality of ultrasound images by automatically determining one or more image quality parameters via a plurality of separate image quality models. In one example, a method for an ultrasound system includes determining a plurality of image quality parameters of an ultrasound image acquired with the ultrasound system, each image quality parameter determined based on output from a separate image quality model, and outputting feedback to a user of the ultrasound system based on the plurality of image quality parameters.

20 Claims, 4 Drawing Sheets

(56) References Cited

U.S. PATENT DOCUMENTS

2020/0060660 A1\* 2/2020 Waechter-Stehle ......................... A61B 8/0858
2020/0327457 A1\* 10/2020 Cmielowski ........... G06N 20/20

OTHER PUBLICATIONS

Rahmatullah, B. et al., "Integration of Local and Global Features for Anatomical Object Detection in Ultrasound," Proceedings of the 15th International Conference on Medical Image Computing and Computer-Assisted Intervention (MICCAI 2012), Oct. 1, 2012, Nice, France, 8 pages.

Zhang, L. et al., "Automatic image quality assessment and measurement of fetal head in two-dimensional ultrasound image," Journal of Medical Imaging, vol. 4, No. 2, Apr. 17, 2017, 11 pages.

\* cited by examiner

SYSTEM AND METHODS FOR ULTRASOUND IMAGE QUALITY DETERMINATION

TECHNICAL FIELD

Embodiments of the subject matter disclosed herein relate to ultrasound imaging, and more particularly, to determining image quality of ultrasound images.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method for an ultrasound system includes determining a plurality of image quality parameters of an ultrasound image acquired with the ultrasound system, each image quality parameter determined based on output from a separate image quality model that is trained to determine a specific image quality metric, and outputting feedback to a user of the ultrasound system based on the plurality of image quality parameters.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Ultrasound images acquired during a medical ultrasound exam may be used to diagnose a patient condition, which may include one or more clinicians analyzing the ultrasound images for abnormalities, measuring certain anatomical features imaged in the ultrasound images, and so forth. Thus, to ensure accurate diagnoses, an ultrasound system operator (e.g., sonographer) may visually inspect acquired ultrasound images and only save ultrasound images of relatively high quality as part of the exam. However, the determination of image quality is subjective and no quantifiable or automated method is currently available to assess image quality. Image quality in ultrasound is also difficult to model and predict quantitatively in a reproducible manner. Further, image quality encompasses a multitude of desirable properties of the image, which are impacted jointly by a combination of factors including acquisition settings, subject-specific properties, and skill of ultrasound system operator. The assessment of the quality of an ultrasound image is often limited to a handful of experts even before a new device or probe is ready for use by clinicians, and is mostly performed in-house by the ultrasound system manufacturer.

Thus, according to embodiments disclosed herein, an artificial intelligence-based framework is provided to compute ultrasound image quality. Specifically, a multitude of models, such as neural networks, are provided, each configured to measure a specific desired property of image quality for a given image, which are aggregated to arrive at a single image quality metric for the image. These models are trained to correlate image content to expert image quality rating, during the training phase and are invoked during inference to predict image quality. In some examples, descriptive evidence of the aggregate prediction may be output (e.g., for display) as well as for the individual neural network outputs, making the approach an explainable AI solution. The computed image quality rating may be used in a variety of post-applications such as triggering automatic workflows, providing confidence for automated measurements, archival, etc.

The determination of image quality as described herein may be based on the recognition of a set of desired properties of an image, including image content specific to a view, overall image noise levels, image contrast, imaging artifacts, and speckle characteristics. Thus, each of these attributes of an ultrasound image may be modeled/determined as a separate neural network and the final image quality metric may be computed as a summation, average, or weighted average of the scores generated by the these multiple networks. Along with prediction of image quality, the system disclosed herein may also provide descriptive feedback regarding the model output, which may help explain how the image quality determination was made, which may assist an ultrasound system operator in quickly acquiring a high quality image.

Figure 1:
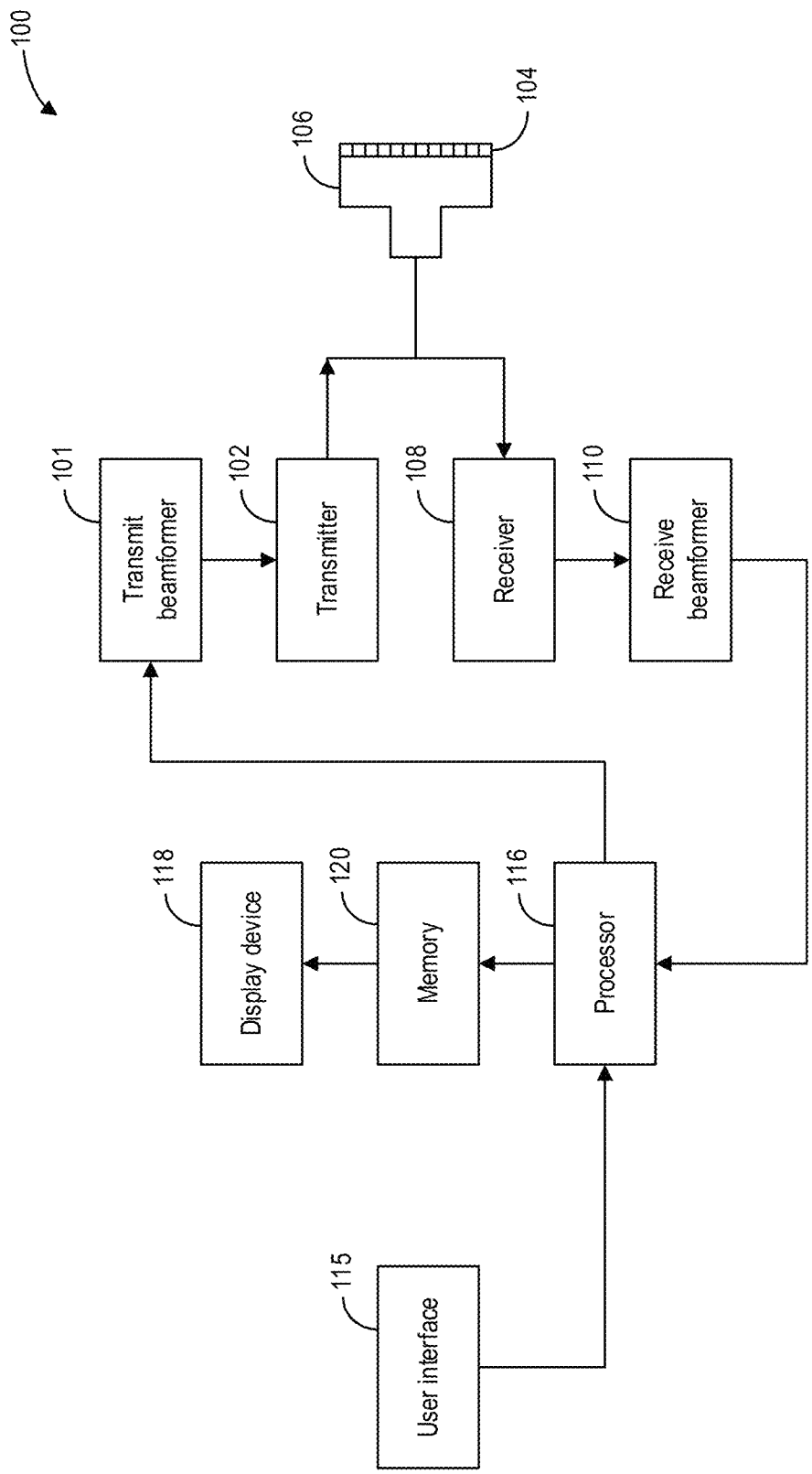
FIG. 1 shows a block diagram of an exemplary embodiment of an ultrasound system.
Figure 2:
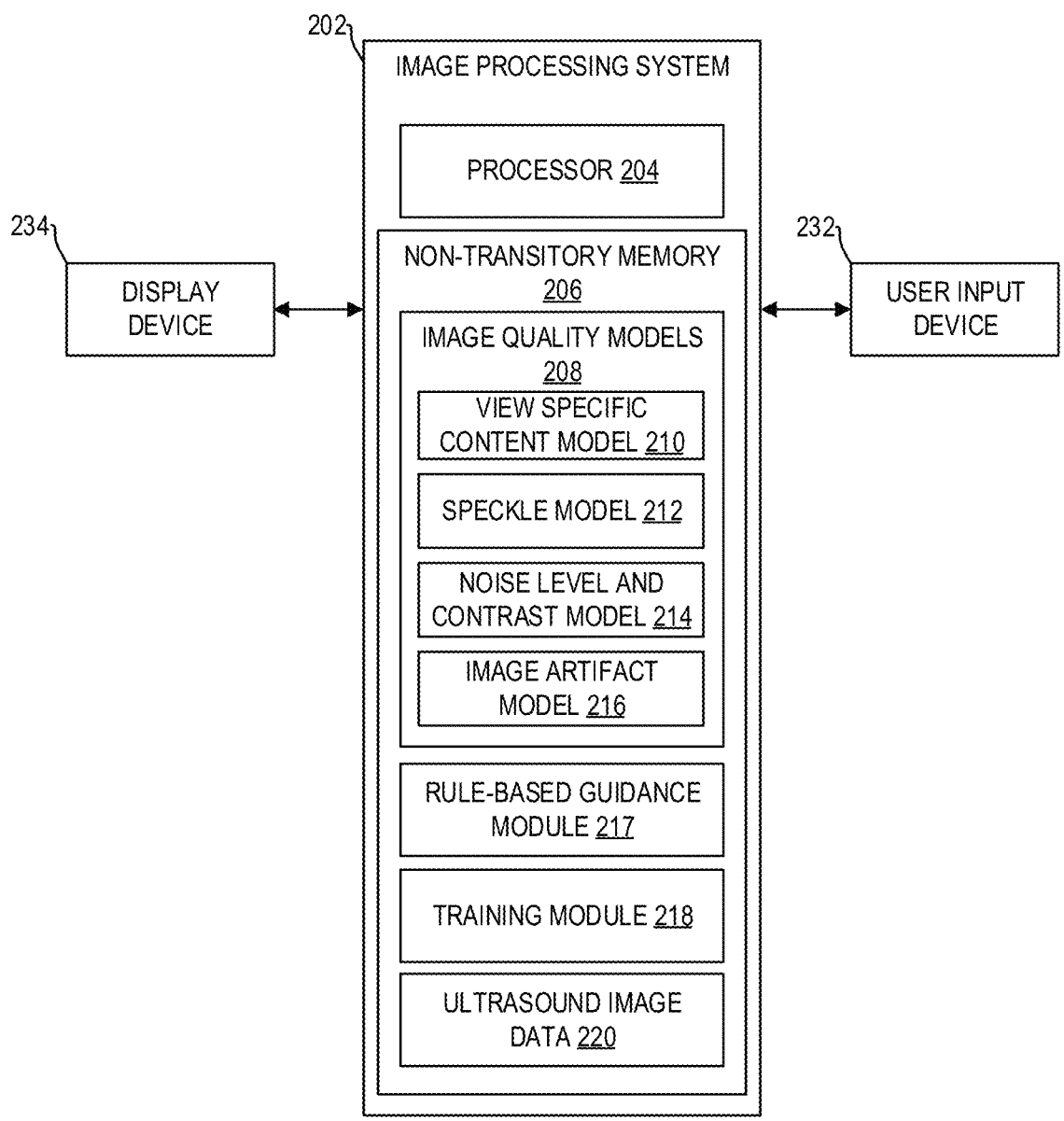
FIG. 2 is a schematic diagram illustrating a system for determining image quality of ultrasound images, according to an exemplary embodiment.
Figure 4:
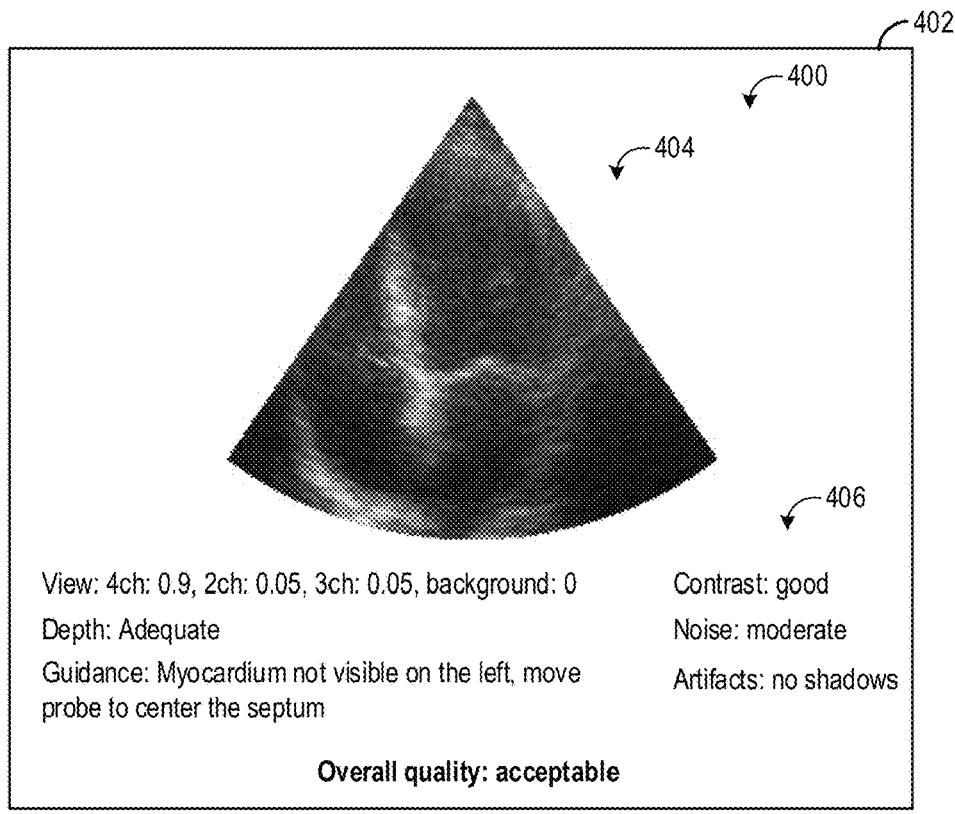
FIG. 4 shows an example graphical user interface displaying ultrasound image quality metrics for a first image.
Figure 5:
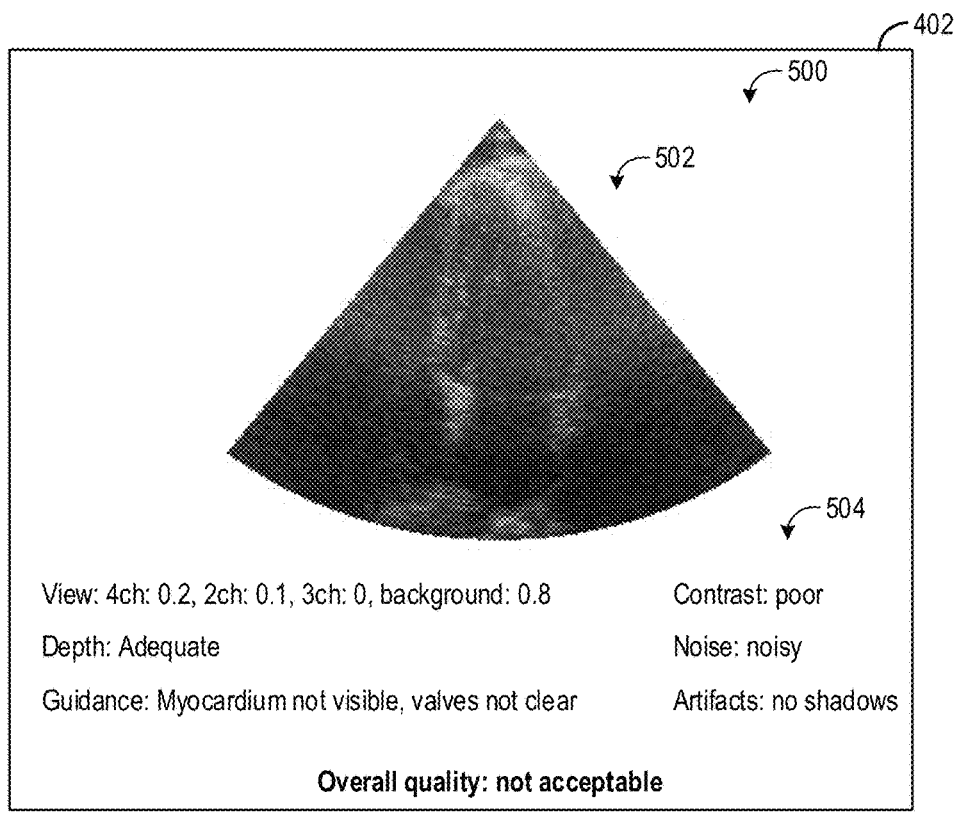
FIG. 5 shows an example graphical user interface displaying ultrasound image quality metrics for a second image.

An example ultrasound system including an ultrasound probe, a display device, and an imaging processing system are shown in FIG. 1. Via the ultrasound probe, ultrasound images may be acquired and displayed on the display device. An image processing system, as shown in FIG. 2, includes a plurality of image quality models which may be deployed according to the method shown in FIG. 3 to determine the image quality of one or more ultrasound images acquired by the ultrasound system. Various image quality metrics and/or acquisition guidance may be output for display to an operator of the ultrasound system, as shown in FIGS. 4 and 5, which may assist the ultrasound operator in acquiring a high-quality image.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be segmented by a machine learning model trained using ultrasound images and corresponding ground truth output. As used herein, ground truth output refers to an expected or "correct" output based on a given input into a machine learning model. For example, if a machine learning model is being trained to classify images of cats, the ground truth output for the model, when fed an image of a cat, is the label "cat". In addition, the image processing system may further process the ultrasound images with one or more different machine learning models configured to receive the ultrasound images and output various image quality metrics of the ultrasound images.

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an exemplary embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may be operably/communicatively coupled to a user input device 232 and a display device 234. The user input device 232 may comprise the user interface 115 of the ultrasound imaging system 100, while the display device 234 may comprise the display device 118 of the ultrasound imaging system 100, at least in some examples.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store image quality models 208, training module 218, and ultrasound image data 220. Image quality models 208 may include one or more machine learning models, such as deep learning networks, comprising a plurality of weights and biases, activation functions, loss functions, gradient descent algorithms, and instructions for implementing the one or more deep neural networks to process input ultrasound images. For example, image quality models 208 may store instructions for implementing a view-specific content model 210, a speckle model 212, a noise level and contrast model 214, and/or an image artifact model 216. Each of the image quality models 208 may include one or more neural networks. Image quality models 208 may include trained and/or untrained neural networks and may further include training routines, or parameters (e.g., weights and biases), associated with one or more neural network models stored therein.

Thus, the image quality models 208 described herein may be deployed to provide live feedback to a user during image acquisition, in the form of an image quality metric. The image quality metric is configured to capture different properties of an ultrasound acquisition that contribute to the image being of high diagnostic quality. For example, in a typical cardiac scan, the user starts close to or inside the cardiac region and navigates to a series of standard/well defined cardiac views. At each of the standard cardiac views, certain structural and functional metrics are measured. However, all the measurements/diagnosis decisions depend considerably on the quality of images/cine loops acquired. As described herein, the quality metric may be a consolidated metric that encompasses several factors that can play a part in the final diagnosis. For example, in certain cases, if the user has not arrived at the right view, or is off from the right view by a few degrees to the right view/scan plane, the final measurements may not be accurate or may be difficult to obtain. Similarly, in certain scenarios, an imaging artifact can be perceived as an anomalous region or a shadow region can lead to wrong caliper placement/boundary segmentation. In other scenarios, having the right acquisition parameters is of utmost importance and not using right parameters can lead to sub-optimal results and misdiagnosis. The described image quality metric tries to capture all these factors and provides a live summary to the user during the scanning process.

View-specific content model 210 may be a neural network or other suitable deep learning or other machine learning model. View-specific content model 210 may be trained to segment anatomical features from background in ultrasound images and identify the segmented anatomical features. In some examples, view-specific content model 210 may use a retina net architecture and may be trained using ultrasound images and/or cine loops that have been annotated by experts, thus identifying anatomical features present in each training ultrasound image. View-specific content model 210 may output a confidence level that a given input ultrasound image is a specified scan plane or view. For example, when view-specific content model 210 is trained on cardiac ultrasound images, view-specific content model 210 may be configured to output a confidence level that an input ultrasound image is a four-chamber view, a three-chamber view, or a two-chamber view. Further, in some examples, view-specific content model 210 may output an indication of where one or more identified target anatomical features are located in an input ultrasound image relative to where those target anatomical features are supposed to be located in a target scan plane. For example, view-specific content model 210 may be configured to output an indication that a septum of a heart in an input ultrasound image is not located in a center of the ultrasound image. The view specific content model may comprise of one or more models, and the one or more models of the view specific content model outputs a confidence score of the view belonging to one of the four standard cardiac views. The confidence score may be indicative of how close a given image is to a view. The view specific content model may be trained as a regression model with the ground truth values signifying the chance of a given image belonging to the standard view.

Speckle model 212 may include a neural network or other suitable deep learning or other machine learning model. Speckle model 212 may be trained to measure resolution in input ultrasound images by using speckle in the images as a marker of resolution. To determine the speckle-based resolution, speckle model 212 may be trained to identify a homogenous region in an image (e.g., inside a left ventricle) and a heterogeneous region in the image (e.g., the septum-left ventricle interface) and then classify the image as high resolution, low resolution, etc., based on speckling in each of the identified regions. In some examples, speckle model 212 may use a U-net or other convolutional neural network architecture to identify the homogenous and heterogeneous regions and may be trained using ultrasound images and/or cine loops where homogenous and/or heterogeneous regions have been annotated/identified by experts. Speckle model 212 may then measure a histogram of oriented gradients at each identified region and classify images (e.g., as high resolution, moderate resolution, or low resolution) based on the histogram. For example, for an ideal image, a robust gradient at the interface of the heterogeneous region may be expected, with minimal variance in the homogeneous region. A histogram of oriented gradients is a machine learning feature that computes gradients in a given region and measures statistics on the computed gradients. For the speckle model, the gradients are expected to have certain amplitude and directionality for a high quality/resolution image, resulting in discrete peaks in the gradient histogram, where as in the low quality/low resolution image, the gradient histogram is expected to have equal distribution across all directions.

Noise level and contrast model 214 may include a neural network to model overall image noise parameters and image contrast. The noise level and contrast model 214 may distinguish images with good contrast and low noise from images with poor contrast and high noise, which may be determined at a global image level and is independent of the image content. Image artifact model 216 may include a neural network to classify/localize shadows and/or other artifacts, such as haze. Image artifact model 216 may be trained using ultrasound images and/or cine loops that have been annotated by experts to identify shadows, reverberation, or other artifacts present in the training ultrasound images. Image artifact model 216 may output an identification and/or location of detected artifacts and/or may output a quantifiable indicator of the level of artifacts present in an input ultrasound image. The presence of artifacts in an image may be quantified by the image artifact model as either binary (e.g., presence or absence) or a value that represents the extent of artifacts as a percentage of the image field of view, for example.

Non-transitory memory 206 may include a rule-based guidance module 217 configured generate guidance output based on the output of the image quality models 208. For example, rule-based guidance module 217 may compare the quality quantifications on a given image (e.g., the output from the image quality models when the given image is input into the image quality models) to optimal configurations and produce guidance output based on rules stored in the rule-based guidance module 217. As an example, the rule-based guidance module 217 may analyze the output of the view specific content model 210 for an image of a given view to determine if the anatomical features for the given view specified by the rules stored in the rule-based guidance module 217 are present in the image and at the location(s) specified by the rules. If not, the rule-based guidance module 217 may output guidance (e.g., to move the ultrasound probe in a certain direction and/or by a certain amount) that may be displayed to the user.

Non-transitory memory 206 may further include training module 218, which comprises instructions for training one or more of the machine learning models stored in image quality models 208. In some embodiments, the training module 218 is not disposed at the image processing system 202. The image quality models 208 thus includes trained and validated network(s).

Non-transitory memory 206 may further store ultrasound image data 220, such as ultrasound images captured by the ultrasound imaging system 100 of FIG. 1. The ultrasound image data 220 may comprise ultrasound image data as acquired by the ultrasound imaging system 100, for example. Further, ultrasound image data 220 may store ultrasound images, ground truth output, iterations of machine learning model output, and other types of ultrasound image data that may be used to train the image quality models 208, when training module 218 is stored in non-transitory memory 206. In some embodiments, ultrasound image data 220 may store ultrasound images and ground truth output in an ordered format, such that each ultrasound image is associated with one or more corresponding ground truth outputs. However, in examples where training module 218 is not disposed at the image processing system 202, the images/ground truth output usable for training the image quality models 208 may be stored elsewhere.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to indicate or label a position of an interventional device in the ultrasound image data 220, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
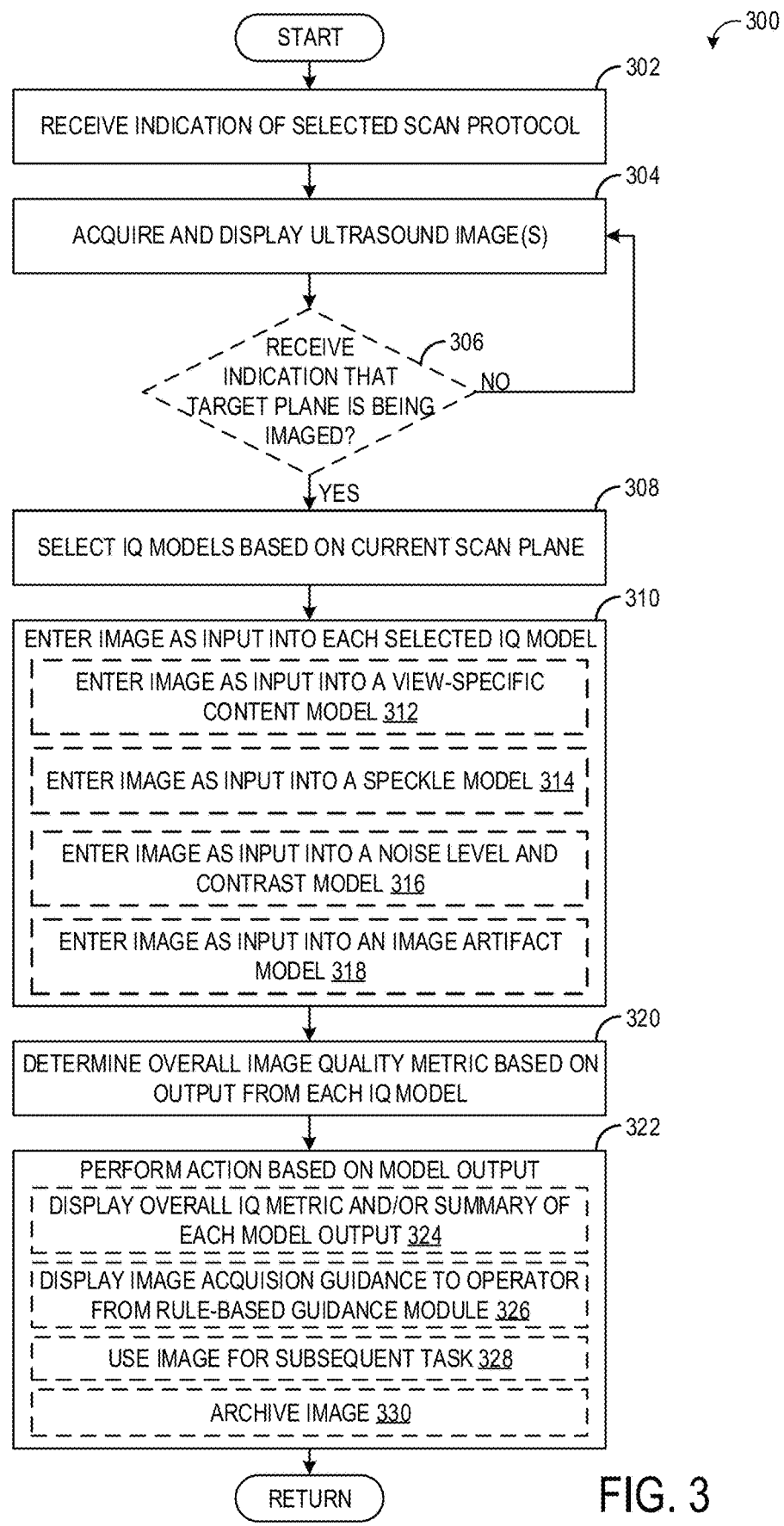
FIG. 3 is a flow chart illustrating a method for determining ultrasound image quality, according to an exemplary embodiment.

FIG. 3 shows a flow chart illustrating an example method 300 for determining image quality of an ultrasound image according to an embodiment. In particular, method 300 relates to inputting an acquired ultrasound image into each of a plurality of image quality models. Each image quality model is trained to output a different, specific image quality metric, such as presence of expected structures, noise/contrast, image artifacts, etc. The output of the image quality models may be presented to an operator of the ultrasound system, which may aid the operator in acquiring high-quality ultrasound images. Method 300 is described with regard to the systems and components of FIGS. 1-2, though it should be appreciated that the method 300 may be implemented with other systems and components without departing from the scope of the present disclosure. Method 300 may be carried out according to instructions stored in non-transitory memory of a computing device, such as image processing system 202 of FIG. 2.

At 302, an indication of a selected scan protocol may be received. The scan protocol may be selected by an operator of the ultrasound system, and may indicate which anatomical features are to be imaged in the ultrasound exam, the goal of the ultrasound exam, information about the patient being scanned (e.g., age, gender, height/weight), and so forth. At 304, ultrasound images are acquired via an ultrasound system (e.g., system 100 of FIG. 1) and displayed on a display device (e.g., display device 118 of FIG. 1). To acquire the images, an ultrasound probe of the ultrasound system (e.g., probe 106) may be controlled to output ultrasound signals (e.g., via energization of the ultrasound transducers of the ultrasound probe) to an imaging subject (such as a patient) and receive the resultant echoes (e.g., where the output acoustic signals are backscattered from the imaging subject). The signals received by the ultrasound probe are then processed by the ultrasound system to generate the ultrasound images that are output for display. The ultrasound images may be acquired and displayed at a suitable frame rate, such as 30 Hz.

At 306, method 300 optionally includes determining if an indication that a target scan plane is being imaged has been received. For example, the operator of the ultrasound system may enter user input (e.g., via user interface 115) indicating which scan plane is currently being imaged and/or which scan plane the operator desires to image. The scan plane the operator desires to image may be dictated by the scan protocol, at least in some examples. For example, during a cardiac scan, images in multiple scan planes may be acquired, such as a four-chamber view plane, a two-chamber view plane, a parasternal long axis (PLAX) view plane, etc. The determination of whether an indication that a target scan plane is being imaged has been received at 306 may be optional, and thus in some examples, method 300 may proceed to 308 regardless of the current scan plane.

If an indication that a target scan plane is being imaged has not been received, method 300 may proceed back to 304 to continue to acquire ultrasound images. If an indication has been received that a target scan plane is being imaged, or if 306 is not performed, method 300 proceeds to 308 to select a set of image quality models based on the current scan plane. As will be explained in more detail below, an ultrasound image may be input into each of a plurality of image quality models that are trained to determine respective different and separate aspects of image quality. In some examples, the image quality models may be trained on a specific scan plane or anatomical view. For example, one of the image quality models may be a speckle model that determines a relative level of speckling present in the ultrasound image. To determine the level of speckling, the speckle model may be trained to identify and segment out various regions of interest in the ultrasound image to measure speckle size, smoothness, and noise levels. Different speckle models may be trained to identify and segment out different regions of interest based on the scan plane in the ultrasound image. Thus, appropriate speckle model that is to be deployed to measure speckle in the current ultrasound image may be selected, from amongst a plurality of different speckle models, based on the scan plane of the current ultrasound image. For each image quality model that is be deployed to determine the image quality of the current ultrasound image, an appropriately trained version of that image quality model may be selected and included as part of the set of image quality models.

The scan plane of the current ultrasound image may be determined via operator input identifying the scan plane in the current ultrasound image. In other examples, the scan plane may be determined automatically based on output from a model trained to identify anatomical features present in the ultrasound image and determine the scan plane of the ultrasound image based on the identified anatomical features. In one example, the view-specific content model (e.g., the view-specific content model 210 of FIG. 2) that is explained in more detail below may be configured to determine the scan plane of the ultrasound image. In still further examples, the selection of the image quality models at 308 may be dispensed with, as the image quality models may be configured to determine the various image quality metrics described herein without an explicit pre-determination of the scan plane of the ultrasound image and/or selection of corresponding, scan plane-specific models.

At 310, the ultrasound image is input into each of a plurality of image quality models, which may be the selected image quality models when 308 is performed. Inputting the ultrasound image into each of a plurality of image quality models includes inputting the ultrasound image into a view-specific content model at 312. The view-specific content model, such as view-specific content model 210 of FIG. 2, may be trained to measure view-specific content that accurately describes the current scan plane. For example, the view-specific content model may determine whether the four chambers of the heart are clearly seen, whether the myocardium is visible, whether the valves for clearly distinguished, whether the apex is visible, and so forth. In some examples, the view-specific content model may output a confidence level that the ultrasound image is a specific view, such as a confidence level (e.g., on a scale of 0-1) that the ultrasound image is a four-chamber view, a confidence level that the ultrasound image is a three-chamber view, and a confidence level that an ultrasound image is a two-chamber view.

Inputting the ultrasound image into each of a plurality of image quality models includes inputting the ultrasound image into a speckle model at 314. The speckle model, such as speckle model 212 of FIG. 2, may extract regions of interest in the ultrasound image, such as a homogenous region (e.g., the left ventricle) and a heterogeneous region (e.g., the septum) and measure speckle properties in the two regions and/or at the interface between the two regions (e.g., speckle size, smoothness, noise in the left ventricle region and at the septum-left ventricle interface). Based on the speckle properties, the speckle model may classify the image on a scale of noise level, e.g., as not noisy, moderately noisy, or severely noisy.

Inputting the ultrasound image into each of a plurality of image quality models includes inputting the ultrasound image into a noise level and contrast model at 316. The noise level and contrast model, such as noise and contrast level model 214 of FIG. 2, may determine an overall noise level and image contrast level for the ultrasound image as a whole. Inputting the ultrasound image into each of a plurality of image quality models includes inputting the ultrasound image into an image artifact model at 318. The image artifact model, such as image artifact model 216, may identify, classify, and/or localize certain image artifacts that may be present in the ultrasound image, such as shadows, reverb, etc.

At 320, an overall image quality metric may be determined based on the output from each image quality model. For example, the output from each image quality model may be quantified (e.g., on a scale from 0-1, on a scale of 1-5, etc.) to reflect numerically the level of image quality for the specific parameter or parameters assessed by the image quality model. The numeric output from each image quality model may be summed or averaged to determine the overall image quality metric.

At 322, an action is performed based on the output from the image quality models. The action that is performed may depend on the image quality determined by the output of the image quality models, the specific scan protocol being carried out, the scan plane of the ultrasound image, operator input, and so forth. As one example, performing the action may include, as indicated at 324, displaying the overall image quality metric determined at 320 and/or a summary of the output of each image quality model. An example graphical user interface that may be displayed to an operator of the ultrasound system, including acquired images and associated image quality output, is shown in FIGS. 4 and 5 and explained in more detail below.

As another example, performing the action may include displaying image acquisition guidance to the operator of the ultrasound system, as indicated at 326. The image acquisition guidance may include instructions to move the ultrasound probe in order to bring one or more anatomical features into view, instructions to adjust ultrasound probe transmit properties to increase image quality (e.g., adjust frequency and/or depth), or other types of guidance that may assist the operator in obtaining ultrasound images with higher image quality. The image acquisition guidance may be generated by a rule-based guidance module, such as rule-based guidance module 217 described above. The rule-based guidance module may apply one or more rules to the output from one or more or each of the image quality models in order to generate the image acquisition guidance.

As a still further example, performing the action may include using the ultrasound image for a subsequent task, as indicated at 328. For example, if the overall image quality metric of the ultrasound image is above a threshold, or if the output from one or more of the image quality models indicates that one or more target anatomical features are sufficiently visible in the ultrasound image, noise is low, etc., the ultrasound image may be used in subsequent downstream processes, such as triggering an automatic workflow, providing confidence for automated measurements, etc. As an example, if the overall image quality metric is above a threshold and the view-specific content model indicates that the ultrasound image adequately images the PLAX view, automated or semi-automated measurements in the PLAX view may be carried out, such as measuring volume, ejection fraction, etc.

As a still further example, performing the action may include archiving the ultrasound image, as indicated at 330. Archiving the ultrasound image may include sending the ultrasound image to a suitable permanent storage location, such as a picture archiving and communication system (PACS). For example, the ultrasound image may be acquired as part of an echocardiogram or other diagnostic exam, where a plurality of ultrasound images of an anatomical region (e.g., the heart) are acquired and saved for later analysis by a clinician for clinical findings. When the system determines that the ultrasound image is of sufficient quality (e.g., an overall image quality metric greater than a threshold, certain desired anatomical features are visible in the ultrasound image, etc.), the ultrasound image may be automatically archived as part of the exam. In other examples, the ultrasound image may only be archived in response to a user request, which in some examples may be entered after the image quality metric and/or model output is displayed to the user. Method 300 then returns.

FIGS. 4 and 5 show examples of a graphical user interface that may be displayed on a display device 402 of an ultrasound system (e.g., display 118 of FIG. 1). A first example 400 of the graphical user interface is shown in FIG. 4. The first example 400 includes a first ultrasound image 404. The first ultrasound image 404 may be input into each of the plurality of image quality models, which may generate output that is displayed along with the first ultrasound image 404 via the graphical user interface. As shown in FIG. 4, the model output may be summarized in an output summary section 406 and includes a summary of the confidence of the scan plane of the first image (e.g., 90% confidence that scan plane is the four-chamber view), a depth metric (adequate), and guidance (indicating that the myocardium is not visible on the left of the image and that the operator could move the probe in order to center the septum in the center of the image). The scan plane view confidence, depth metric, and guidance may all be determined from the output from the view-specific content model. The output summary section 406 further includes a contrast metric (good), a noise metric (moderate), and an artifact metric (no shadows), which may be output from the noise level and contrast model, speckle model, and image artifact model, respectively. The first image is also assigned an overall image quality metric, herein articulated as being acceptable, although other ways of conveying the metric are possible, such as a numeric score.

The view-specific content model may output only the landmarks present and their spatial locations. For a specific view, by using images generated from optimal depth settings (e.g., depth settings that generate a high quality image), the relative spatial landmark locations may be computed and stored, as well as their locations inside the field of view. Another rule-based algorithm (e.g., rule-based guidance module 217 of FIG. 2) may be applied to compare the spatial locations of landmarks of a given image with the optimal spatial configurations of the given view. Depending upon the deviation from optimal configuration, guidance may be provided the user to increase or decrease the depth.

A second example 500 of the graphical user interface is shown in FIG. 5. The second example 500 includes a second ultrasound image 502. The second ultrasound image 502 may be input into each of the plurality of image quality models, which may generate output that is displayed along with the second ultrasound image 502 via the graphical user interface. As shown in FIG. 5, the model output may be summarized in an output summary section 504 and includes a summary of the confidence of the scan plane of the first image (e.g., a low confidence in any of the standard views), a depth metric (adequate), and guidance (indicating that the myocardium is not visible and that the valves are not clear). The scan plane view confidence, depth metric, and guidance may all be determined from the output from the view-specific content model. The output summary section 504 further includes a contrast metric (poor), a noise metric (noisy), and an artifact metric (no shadows), which may be output from the noise level and contrast model, speckle model, and image artifact model, respectively. The second image is also assigned an overall image quality metric, herein articulated as being not acceptable, although other ways of conveying the metric are possible, such as a numeric score.

In order to generate the guidance and/or other information that displayed in FIGS. 4 and 5, a rule-based guidance module may be applied to convert the model outputs to summary/guidance for the users, such as the rule-based guidance module 217 described above.

In this way, an operator of the ultrasound system may be able to quickly determine the image quality of the current ultrasound image in a quantifiable manner that classifies the image quality by definable metrics. This may allow the operator to make adjustments to probe position and/or transmit parameters in order to increase image quality, or to trigger downstream actions if the quality is sufficient.

A technical effect of automatically determining image quality of an ultrasound image is that an operator of an ultrasound system may be notified if image quality is low and/or be given guidance as to how to increase image quality, which may assist in generating higher quality images for exams and increase exam reproducibility. Another technical effect is reduced operator workflow due to automatic detection of image quality and, where applicable, automatic performance of downstream actions based on the image quality.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an ultrasound system, comprising:
   determining a plurality of image quality parameters of an ultrasound image acquired with the ultrasound system, each image quality parameter determined based on output from a separate respective image quality model of a plurality of image quality models, where each image quality model outputs a separate quantifiable image quality metric; and
   outputting feedback to a user of the ultrasound system based on the plurality of image quality parameters, including displaying a summary of the output from one or more of the image quality models on a display device, where the summary includes an overall image quality metric determined by summing or averaging all of the quantifiable image metrics.

2. The method of claim 1, wherein outputting feedback to the user comprises displaying, on a display device, image acquisition guidance that is based on one or more of the plurality of image quality parameters.

3. The method of claim 2, wherein displaying, on the display device, image acquisition guidance that is based on one or more of the plurality of image quality parameters comprises entering output from one or more of the image quality models into a rule-based guidance module configured to generate the image acquisition guidance based on the output from one or more of the image quality models.

4. The method of claim 1, further comprising archiving the ultrasound image and/or triggering a subsequent image-based task based on the plurality of image quality parameters.

5. The method of claim 1, wherein determining each image quality parameter based on output from a separate image quality model comprises determining a first image quality parameter based on output from a view-specific content model and determining a second image quality parameter based on output from a speckle model, wherein the view-specific content model comprises a first neural network and the speckle model comprises a second neural network.

6. The method of claim 5, wherein the output from the view-specific content model comprises an identification of one or more anatomical features in the ultrasound image and/or an identification of a scan plane of the ultrasound image, and wherein the image quality parameter determined from the output of the view-specific content model includes an indication of whether a target anatomical feature is visible in the ultrasound image.

7. The method of claim 5, wherein the output from the speckle model comprises speckle size and/or speckle smoothness of one or more regions of the ultrasound image, and wherein the image quality parameter determined from the output of the speckle model includes a noise level of the ultrasound image.

8. The method of claim 5, wherein determining each image quality parameter based on output from a separate image quality model further comprises determining a third image quality parameter based on output from a contrast model and determining a fourth image quality parameter based on output from an image artifact model, wherein the contrast model comprises a third neural network and the image artifact model comprises a fourth neural network.

9. The method of claim 8, wherein the output from the contrast model comprises a contrast level and a noise level of the ultrasound image and the output from the image artifact model comprises an identification of any artifacts detected in the ultrasound image.

10. A system, comprising:
a display device;
an ultrasound probe;
a memory storing instructions; and
a processor communicably coupled to the memory and when executing the instructions, configured to:
acquire, via the ultrasound probe, an ultrasound image;
determine a plurality of image quality parameters of the ultrasound image, each image quality parameter determined based on output from a separate image quality model, including determining a first image quality parameter based on output from a view-specific content model, the output from the view-specific content model including an identification of one or more anatomical features in the ultrasound image and/or an identification of a scan plane of the ultrasound image, the view-specific content model comprising a first neural network, and determining a second image quality parameter based on output from a speckle model comprising a second neural network, each of the view-specific content model and the speckle model trained with expert-annotated ultrasound images; and
display, on the display device, a representation of the plurality of image quality parameters.

11. The system of claim 10, wherein the representation of the plurality of image quality parameters includes an overall image quality metric that includes a summation or average of a plurality of quantifiable image metrics each representing a respective image quality parameter of the plurality of image quality parameters.

12. The system of claim 10, wherein the representation of the plurality of image quality parameters includes a summary of the output from one or more of the image quality models.

13. The system of claim 10, wherein the processor, when executing the instructions, is configured to display image acquisition guidance that is based on one or more of the plurality of image quality parameters.

14. The system of claim 10, wherein the processor, when executing the instructions, is configured to archive the ultrasound image and/or trigger a subsequent image-based task based on one or more of the plurality of image quality parameters.

15. The system of claim 10, wherein the first image quality parameter determined from the output of the view-specific content model includes an indication of whether a target anatomical feature is visible in the ultrasound image.

16. The system of claim 10, wherein the output from the speckle model comprises speckle size and/or speckle smoothness of one or more regions of the ultrasound image, and wherein the image quality parameter determined from the output of the speckle model includes a resolution of the ultrasound image.

17. The system of claim 10, wherein determining each image quality parameter based on output from a separate image quality model further comprises determining a third image quality parameter based on output from a contrast model and determining a fourth image quality parameter based on output from an image artifact model.

18. The system of claim 17, wherein the image artifact model is trained based on additional expert-annotated ultrasound images annotated to identify artifacts present in the expert-annotated ultrasound images, and wherein the contrast model is trained to distinguish images with good contrast and low noise from images with poor contrast and high noise at a global image level, independent of image content.

19. The system of claim 10, wherein the expert-annotated ultrasound images used to train the view-specific content model are annotated to identify one or more anatomical features present in each expert-annotated ultrasound image, and the expert-annotated ultrasound images used to train the speckle model are annotated to identify homogenous and/or heterogeneous regions in each expert-annotated ultrasound image, and where the speckle model identifies one or more homogenous and/or heterogeneous regions in the ultrasound image and measures a histogram of oriented gradients at each identified homogenous and/or heterogeneous region of the ultrasound image and generates an image quality parameter for the ultrasound image based on the histogram.

20. A method, comprising:
determining a plurality of image quality parameters of an ultrasound image, each image quality parameter determined based on output from a separate image quality model, each image quality model comprising a separate neural network, including a first image quality parameter determined from a view-specific model, a second image quality parameter determined from a speckle model trained to output a speckle size and/or speckle smoothness of one or more regions of the ultrasound image, a third image quality parameter determined from a noise and contrast level model, and a fourth image quality parameter determined from an image artifact model; and
displaying a representation of the plurality of image quality parameters on a display device.

* * * * *